(12) United States Patent
Asami et al.

(10) Patent No.: US 12,740,935 B2
(45) Date of Patent: Sep. 22, 2026

(54) FIBER-FORMING COMPOSITION

(71) Applicant: KAO CORPORATION, Tokyo (JP)

(72) Inventors: Nobuyuki Asami, Odawara (JP); Hikaru Kimura, Wakayama (JP); Hirokatsu Sugawara, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 714 days.

(21) Appl. No.: 18/245,837

(22) PCT Filed: Sep. 9, 2021

(86) PCT No.: PCT/JP2021/033150
§ 371 (c)(1),
(2) Date: Mar. 17, 2023

(87) PCT Pub. No.: WO2022/059591
PCT Pub. Date: Mar. 24, 2022

(65) Prior Publication Data

US 2024/0024223 A1 Jan. 25, 2024

(30) Foreign Application Priority Data

Sep. 18, 2020 (JP) ................................ 2020-157470

(51) Int. Cl.
*A61K 8/891* (2006.01)
*A61K 8/02* (2006.01)
(Continued)

(52) U.S. Cl.
CPC .............. *A61K 8/891* (2013.01); *A61K 8/027* (2013.01); *A61K 8/345* (2013.01); *A61K 8/8135* (2013.01); *A61Q 1/12* (2013.01); *A61K 2800/95* (2013.01)

(58) Field of Classification Search
CPC .............................. A61K 8/027; C23C 18/181
See application file for complete search history.

(56) References Cited

U.S. PATENT DOCUMENTS 5,996,855 A * 12/1999 Alexander ................ B05B 3/02 118/621
6,531,142 B1 3/2003 Rabe et al.
(Continued)

FOREIGN PATENT DOCUMENTS

JP 2003-507165 A 2/2003
JP 2006-104211 A 4/2006
(Continued)

OTHER PUBLICATIONS

WO2019156146A1, machine translation. (Year: 2019).*
International Search Report issued Nov. 16, 2021 in PCT/JP2021/033150, filed on Sep. 9, 2021, 2 pages.

*Primary Examiner* — Robert A Vetere
(74) *Attorney, Agent, or Firm* — Oblon, McClelland, Maier & Neustadt, L.L.P.

(57) ABSTRACT

A method for producing a coating film, including forming a coating film containing a deposit containing fibers on a surface of an object for forming a coating thereon by an electrostatic spray of a composition. The composition includes component (a) a polymer having a coating film forming ability, (b) one or more volatile substances selected from the group consisting of water, an alcohol and a ketone, and (c) an oil component being liquid at 25° C. and containing a component (c1) one or more selected from the group consisting of oil components having a surface tension at 25° C. of 25 mN/m or less and being liquid at 25° C.

14 Claims, 1 Drawing Sheet

(51) Int. Cl.

| | |
|---|---|
| ***A61K 8/34*** | (2006.01) |
| ***A61K 8/81*** | (2006.01) |
| ***A61Q 1/12*** | (2006.01) |

(56) References Cited

U.S. PATENT DOCUMENTS

| | | | |
|---|---|---|---|
| 2019/0053602 | A1 | 2/2019 | Amari et al. |
| 2021/0038530 | A1 | 2/2021 | Yoshino |

FOREIGN PATENT DOCUMENTS

| | | | | |
|---|---|---|---|---|
| JP | 2017-78062 | A | 4/2017 | |
| JP | 2020-063226 | A | 4/2020 | |
| WO | WO 01/12335 | A1 | 2/2001 | |
| WO | WO-2019156146 | A1 * | 8/2019 | ........... C09D 129/14 |

* cited by examiner

FIBER-FORMING COMPOSITION

CROSS REFERENCE TO RELATED APPLICATIONS

This application is a National Stage entry under 35 U.S.C. § 371 of PCT/JP2021/033150, filed on Sep. 9, 2021, and claims priority to Japanese Patent Application No. 2020-157470, filed on Sep. 18, 2020. The entire contents of both are incorporated herein by reference.

FIELD OF THE INVENTION

The present invention relates to a composition for forming a coating film comprising a deposit containing fibers by an electrostatic spray.

BACKGROUND OF THE INVENTION

Various methods are known for forming a coating film by an electrostatic spray. For example, Patent Literature 1 discloses a skin treatment method including electrostatically spraying a composition on the skin. The composition used in this method contains a liquid insulating substance, a conductive substance, a particulate powder substance, and a thickener. This composition is typically used as cosmetic products containing a pigment and skincare compositions. Specifically, the composition is used as a cosmetic foundation. That is, the invention described in Patent Literature 1 primarily envisioned for cosmetic purposes by electrostatically spraying a foundation to cosmetically decorate the skin.

Patent Literature 2 discloses a disposable cartridge to be used for an electrostatic spray apparatus of a cosmetic product. This electrostatic spray apparatus is a hand-held and self-contained style. This electrostatic spray apparatus is used to spray a cosmetic foundation as in Patent Literature 1 described above.

Patent Literature 3 discloses a method for enhancing coating film adhesion by applying a solution to a skin before or after forming a coating film on the surface of the skin by an electrostatic spray method.

[Patent Literature 1] JP-A-2006-104211
[Patent Literature 2] JP-A-2003-507165
[Patent Literature 3] JP-A-2017-78062

SUMMARY OF THE INVENTION

The present invention relates to a fiber formable composition for forming a coating film comprising a deposit containing fibers on a surface of an object for forming a coating thereon by an electrostatic spray, the fiber formable composition comprising the following Components (a), (b), and (c):

(a) a polymer having a coating film forming ability;

(b) one or more volatile substances selected from the group consisting of water, an alcohol and a ketone; and (c) an oil component being liquid at 25° C. and containing (c1) one or more selected from the group consisting of oil components having a surface tension at 25° C. of 25 mN/m or less and being liquid at 25° C., wherein a content of Component (c1) in the entire fiber formable composition is 9% by mass or more and 25% by mass or less, and a mass ratio of Component (c1) to Component (c), ((c1)/(c)), is 0.6 or more.

The present invention also relates to a method for producing a coating film, comprising forming a coating film comprising a deposit containing fibers on a surface of an object for forming a coating thereon by an electrostatic spray using a composition comprising the following Components (a), (b), and (c):

(a) a polymer having a coating film forming ability;

(b) one or more volatile substances selected from the group consisting of water, an alcohol and a ketone; and (c) an oil component being liquid at 25° C. and containing (c1) one or more selected from the group consisting of oil components having a surface tension at 25° C. of 25 mN/m or less and being liquid at 25° C., wherein a content of Component (c1) in the entire fiber formable composition is 9% by mass or more and 25% by mass or less, and a mass ratio of Component (c1) to Component (c), ((c1)/(c)), is 0.6 or more.

DETAILED DESCRIPTION OF THE INVENTION

Figure 1:
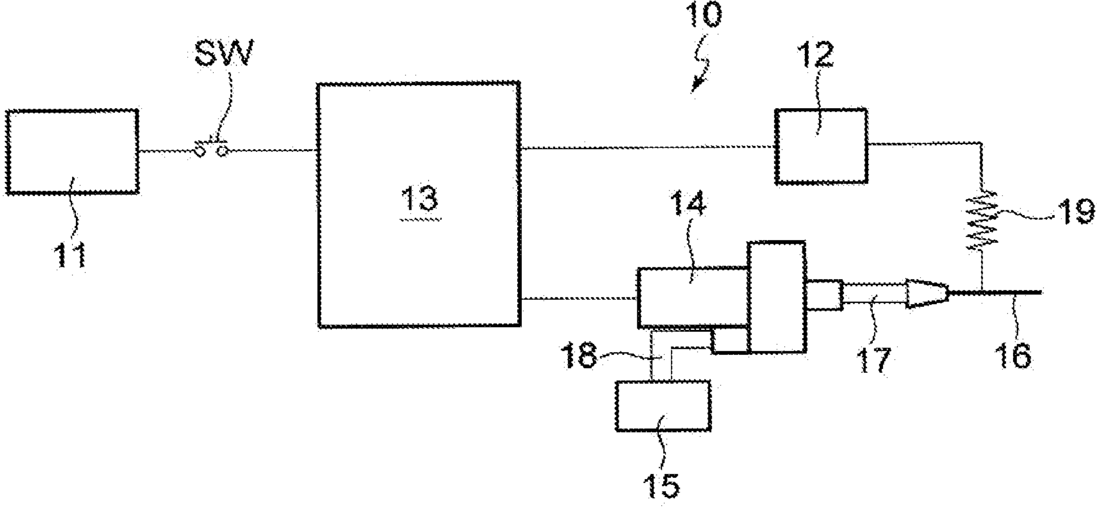
FIG. 1 illustrates a schematic diagram showing a structure of the electrostatic spray apparatus suitably used in the present invention.

When a coating film comprising a fibrous deposit is formed on a surface of an object for forming a coating thereon, such as the skin, by an electrostatic spray in accordance with a method described in Patent Literatures described above, it found that increasing the spray rate results in problems of formation of holes in the fibrous deposits due to droplets, and failure to form fibers.

Accordingly, the present invention relates to a composition with which fibers are successfully formed and a coating film comprising a fibrous deposit can be efficiently formed on a surface of an object for forming a coating thereon even at a high spray rate.

Therefore, the present inventors made various investigations on the composition of an electrostatic spray composition used for forming a coating film, and consequently found that, when a prescribed amount of a liquid oil having a specific surface tension is used in addition to a polymer having a coating film forming ability and a volatile substance, fibers are successfully formed by an electrostatic spray, and a coating film comprising a fibrous deposit can be efficiently formed on a surface of an object for forming a coating thereon even if spray rate is high, thereby completing the present invention.

When a coating film is formed on a surface of an object for forming a coating thereon by an electrostatic spray using the composition of the present invention, even if spray rate is high, fibers are successfully formed, and a coating film comprising a fibrous deposit can be efficiently formed on the surface of the object for forming a coating thereon. Besides, the thus obtained coating film is formed as a uniform coating film comprising a fibrous deposit, and hence has, when applied to the skin, a favorable elastic modus and is excellent in skin compatibility, adhesion, followability to motion of the skin, and durability against moisture.

A fiber formable composition of the present invention is a composition for forming a coating film comprising a fibrous deposit on a surface of an object for forming a coating thereon, such as the skin, by an electrostatic spray, and comprises the above-described Components (a), (b) and (c). It notes that a "coating film comprising a fibrous deposit" of the present invention means a coating film comprising a fibrous deposit formed of Component (a), and a liquid substance may be present in a portion excluding fibers, for example, around the fibers. The electrostatic spray is preferably electrospinning. The fiber formable composition of the present invention is preferably a fiber formable composition for the skin.

In the polymer having a coating film forming ability as Component (a) is generally a substance soluble in the volatile substance as Component (b). Soluble herein refers to a state in which, when Component (a) and Component (b) are mixed, Component (a) is in a dispersed state in Component (b) at 20° C. and such a dispersed state is a visually homogenous state, and preferably a visually transparent or semitransparent state. The coating film forming ability of the present invention is preferably fiber forming ability.

For the polymer having a coating film forming ability, a suitable polymer is used depending on the property of the volatile substance of Component (b). Specifically, the polymers having a coating film forming ability are roughly categorized into water-soluble polymers and water-insoluble polymers. The "water-soluble polymer" in the present Description refers to a polymer having a property that, after weighing 1 g of the polymer under an environment of 1 atmosphere and 23° C., the polymer is immersed in 10 g of ion exchange water, and after having passed 24 hours, 0.5 g or more of the immersed polymer is dissolved in water. On the other hand, the "water-insoluble polymer" in the present Description refers to a polymer having a property that, after weighing 1 g of the polymer under an environment of 1 atmosphere and 23° C., the polymer is immersed in 10 g of ion exchange water, and after having passed 24 hours, only less than 0.5 g of the immersed polymer is dissolved in water.

Examples of the water-soluble polymer having a coating film forming ability include mucopolysaccharides such as pullulan, hyaluronic acid, chondroitin sulfate, poly-γ-glutamic acid, modified cornstarch, β-glucan, glucooligosaccharide, heparin, and keratosulfate, natural macromolecules such as cellulose, pectin, xylan, lignin, glucomannan, galacturonic acid, psyllium seed gum, tamarind seed gum, gum arabic, gum tragacanth, water-soluble soybean polysaccharide, alginic acid, carrageenan, laminaran, agarose, fucoidan, methyl cellulose, hydroxypropyl cellulose, and hydroxypropyl methylcellulose, synthetic macromolecules such as a partially saponified polyvinyl alcohol (when not used in combination with a crosslinking agent), a low saponified polyvinyl alcohol, polyvinylpyrrolidone (PVP), polyethylene oxide, and sodium polyacrylate. These water-soluble polymers can be used singly or two or more can be used in combination. Of these water-soluble polymers, it is preferable to use pullulan, and synthetic macromolecules such as a partially saponified polyvinyl alcohol, a low saponified polyvinyl alcohol, polyvinylpyrrolidone, and polyethylene oxide from a viewpoint of easy production of a coating film. When polyethylene oxide is used as the water-soluble polymer, a number average molecular weight thereof is preferably 50,000 or more and 3,000,000 or less, and more preferably 100,000 or more and 2,500,000 or less.

Meanwhile, examples of the water-insoluble polymer having a coating film forming ability include a completely saponified polyvinyl alcohol insolubilizable after a coating film is formed, a partially saponified polyvinyl alcohol crosslinkable after a coating film is formed when used in combination with a crosslinking agent, oxazoline-modified silicones such as a poly(N-propanoylethyleneimine)graft-dimethylsiloxane/γ-aminopropylmethylsiloxane copolymer, a polyvinyl acetal diethylamino acetate, Zein (main component of corn protein), a polyester resin such as polylactic acid (PLA), an acrylic resin such as a polyacrylonitrile resin and a polymethacrylic acid resin, and a polystyrene resin, a polyvinyl butyral resin, a polyethylene terephthalate resin, a polybutylene terephthalate resin, a polyurethane resin, a polyamide resin, a polyimide resin, and a polyamideimide resin. One of these water-insoluble polymers can be singly used, or two or more of these can be used in combination.

Of these water-insoluble polymers, it is preferable to use a completely saponified polyvinyl alcohol insolubilizable after a coating film is formed, a partially saponified polyvinyl alcohol crosslinkable after a coating film is formed when used in combination with a crosslinking agent, a polyvinyl butyral resin, a polyurethane resin, and oxazoline-modified silicones such as a poly(N-propanoylethyleneimine)graft-dimethylsiloxane/γ-aminopropylmethylsiloxane copolymer, a polyvinyl acetal diethylamino acetate, and Zein.

Component (a) is preferably a polymer dissolved or dispersed in Component (b) described below, preferably a water-insoluble polymer having a coating film forming ability, and more preferably one or more selected from the group consisting of a partially saponified polyvinyl alcohol, a low saponified polyvinyl alcohol, a completely saponified polyvinyl alcohol, a polyvinyl butyral resin, a polyurethane resin, a polymethacrylic acid resin, an oxazoline-modified silicone, a polyvinyl acetal diethylamino acetate, and a polylactic acid.

A content of Component (a) in the fiber formable composition of the present invention is preferably 4 mass % or more, more preferably 5 mass % or more, further more preferably 6 mass % or more, and even more preferably 8 mass % or more. Additionally, it is preferably 35 mass % or less, more preferably 30 mass % or less, further more preferably 25 mass % or less, and even more preferably 20 mass % or less. A content of Component (a) in the fiber formable composition is preferably 4 mass % or more and 35 mass % or less, more preferably 4 mass % or more and 30 mass % or less, further more preferably 6 mass % or more and 25 mass % or less, and even more preferably 8 mass % or more and 20 mass % or less. When Component (a) is contained in the fiber formable composition in this proportion, a coating film comprising a fibrous deposit containing Component (a) as a principal component or skeleton can be efficiently formed by an electrostatic spray, and in addition, the coating film formed of fibers can be stably formed.

The volatile substance as Component (b) is one or more volatile substances selected from the group consisting of water, an alcohol, and a ketone. Component (b) in the fiber formable composition is blended for the purpose of finally forming a dry coating film, wherein the fiber formable composition placed within the electric field is sufficiently charged, subsequently discharged toward the skin from a nozzle tip, a charge density of the fiber formable composition becomes excess as Component (b) evaporates, and Component (b) further evaporates while broken down by Coulomb repulsion. For this purpose, the volatile substance has a vapor pressure at 20° C. of preferably 0.01 kPa or more and 106.66 kPa or less, more preferably 0.13 kPa or more and 66.66 kPa or less, further more preferably 0.67 kPa or more and 40.00 kPa or less, further more preferably 1.33 kPa or more and 40.00 kPa or less, and even more preferably 2.40 kPa or more and 40.00 kPa or less.

The volatile substance as Component (b) preferably contains one or more selected from the group consisting of water, an alcohol, and a ketone.

For example, monovalent chain fatty alcohols, monovalent cyclic fatty alcohols, and monovalent aromatic alcohols are preferably used as the alcohol. Examples of the monovalent chain fatty alcohol include straight chain or branched chain alcohols having 1 to 6 carbon atoms, examples of the monovalent cyclic fatty alcohol include cyclic fatty alcohols having 4 to 6 carbon atoms, and examples of the monovalent aromatic alcohol include benzyl alcohol and phenyl ethyl alcohol. Specific examples thereof include methanol, ethanol, isopropyl alcohol, n-propyl alcohol, n-butyl alcohol, 2-butyl alcohol, isobutyl alcohol, 2-methyl-2-propyl alcohol, n-pentanol, 2-pentanol, 3-pentanol, 2-methyl-1-butyl alcohol, 2-methyl-2-butyl alcohol, 3-methyl-1-butyl alcohol, 3-methyl-2-butyl alcohol, neopentyl alcohol, n-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, 2-ethyl-1-butanol, cyclobutanol, cyclopentanol, cyclohexanol, benzyl alcohol, and phenylethyl alcohol. These alcohols selected therefrom can be used singly or in combinations of two or more.

Of the volatile substances as Component (b), examples of the ketone include ketones having two alkyl groups having 1 to 4 carbon atoms such as acetone, methyl ethyl ketone, and methyl isobutyl ketone. These ketones can be used singly or two or more can be used in combination.

As the volatile substance of Component (b), one, or a combination of two or more selected from the group consisting of the alcohols and the ketones can preferably be used, and water may be further contained.

The volatile substance as Component (b) is more preferably one or more selected from the group consisting of water, ethanol, isopropyl alcohol, and n-butyl alcohol, further more preferably one or more selected from the group consisting of water, ethanol, and isopropyl alcohol, and even more preferably water and ethanol. Here, water may be contained in a content of 0.4% by mass or more and 10% by mass or less with respect to a total content of Component (b).

A total content of Component (b) in the fiber formable composition is preferably 30 mass % or more, more preferably 35 mass % or more, further more preferably 40 mass % or more, and even more preferably 45 mass % or more from a viewpoint of fiber formability. The content is preferably 87 mass % or less, more preferably 86 mass % or less, further more preferably 84 mass % or less, and even more preferably 82 mass % or less. From the same viewpoint, the total content of Component (b) in the fiber formable composition is preferably 30 mass % or more and 87 mass % or less, more preferably 35 mass % or more and 86 mass % or less, further more preferably 40 mass % or more and 84 mass % or less, and even more preferably 45 mass % or more and 82 mass % or less. When Component (b) is contained in this proportion in the fiber formable composition, an intended coating film can be efficiently formed and a coating film composed of fibers can be formed stably. When Component (b) is contained in this proportion in the fiber formable composition, Component (b) can be efficiently and sufficiently volatilized from the fiber formable composition when carrying out the electrostatic spray method. Here, the total content of Component (b) refers to, for example, a total content of an alcohol and water, and preferably a total content of ethanol and water.

A content mass ratio of Component (a) to Component (b) in the fiber formable composition, ((a)/(b)), is, from a viewpoint of efficiently forming a desired coating film, from a viewpoint of stably forming the coating film composed of fibers, and from a viewpoint of efficiently and sufficiently volatilizing Component (b) from the fiber formable composition in carrying out the electrostatic spray method, preferably 0.03 or more, more preferably 0.05 or more, further more preferably 0.08 or more, further more preferably 0.1 or more, and even more preferably 0.12 or more. Additionally, from the same viewpoints, it is preferably 0.6 or less, more preferably 0.45 or less, further more preferably 0.35 or less, further more preferably 0.3 or less, further more preferably 0.25 or less, further more preferably 0.2 or less, and even more preferably 0.18 or less. Such (a)/(b) is preferably 0.03 or more and 0.6 or less, more preferably 0.05 or more and 0.45 or less, further more preferably 0.08 or more and 0.35 or less, further more preferably 0.1 or more and 0.3 or less, and even more preferably 0.12 or more and 0.25 or less.

Component (c) is, as a whole, an oil component being liquid at 25° C., and contains (c1) one or more selected from the group consisting of oil components having a surface tension at 25° C. of 25 mN/m or less and being liquid at 25° C. This Component (c) is a component with which fibers are successfully formed and a coating film comprising a fibrous deposit can be efficiently formed on a surface of an object for forming a coating thereon when used in combination with Components (a) and (b) described above even if spray rate employed at the time of electrostatic spray is high.

The oil component being liquid at 25° C. as a whole as Component (c) contains (c1) one or more selected from the group consisting of oil components having a surface tension at 25° C. of 25 mN/m or less and being liquid at 25° C.

A surface tension can be measured by Wilhelmy method (plate method). A surface tension can be measured, for example, with an automatic surface tensiometer KRUSSK100.

Each parenthesized surface tension mentioned in specific examples below is a value measured at 25° C. for 60 seconds, and shows an average of five measured values.

Besides, the surface tension at 25° C. of Components (c1) is preferably 5 mN/m or more and 25 mN/m or less, more preferably 10 mN/m or more and 25 mN/m or less, and further more preferably 10 mN/m or more and 23 mN/m or less from the viewpoint that fibers are successfully formed and a coating film comprising a fibrous deposit is efficiently formed on an object for forming a coating thereon even if spray rate employed at the time of electrostatic spray is high.

From the viewpoint that fibers are successfully formed and a coating film comprising a fibrous deposit is efficiently formed on a surface of an object for forming a coating thereon even if spray rate employed at the time of electrostatic spray is high, Component (c1) is preferably a silicone oil, a fluorine oil, or a fluorine-modified silicone being liquid at 25° C. and having a surface tension at 25° C. of 25 mN/m or less, more preferably a silicone oil having a surface tension at 25° C. of 25 mN/m or less, and further more preferably a volatile silicone oil being liquid at 25° C. Being volatile refers to having a flash point of from 35 to 87° C. Specific examples (each having a parenthesized surface tension) include methyl trimethicone (17.2 mN/m), dimethyl polysiloxane 0.65CS (15.9 mN/m), dimethyl polysiloxane 1CS (16.9 mN/m), dimethyl polysiloxane 1.5CS (17.7 mN/m), dimethyl polysiloxane 2CS (18.3 mN/m), dimethyl polysiloxane 5CS (19.7 mN/m), dimethyl polysiloxane 6CS (19.8 mN/m), perfluoropolyether (17.2 mN/m) manufactured by Fomblin, and perfluoroalkyl-modified silicone (18.8 mN/m).

From the viewpoint that fibers are successfully formed and a coating film comprising a fibrous deposit is efficiently formed on a surface of an object for forming a coating thereon even if spray rate employed at the time of electrostatic spray is high, the content of Component (c1) is 9% by mass or more and 25% by mass or less in the whole fiber formable composition, and from the same viewpoint, is preferably 10% by mass or more and preferably 22% by mass or less, and more preferably 20% by mass or less. Specifically, the content is preferably 10% by mass or more and 22% by mass or less, and more preferably 10% by mass or more and 20% by mass or less.

A portion of Component (c) excluding Component (c1) is not particularly limited as long as it is an oil component being liquid at 25° C., and examples include an ester oil being liquid at 25° C., a hydrocarbon oil being liquid at 25° C., a higher alcohol being liquid at 25° C., and a fatty acid being liquid at 25° C., different from Component (c1).

Among these, an ester oil being liquid at 25° C., a hydrocarbon oil being liquid at 25° C., and a higher alcohol being liquid at 25° C. are more preferred from the viewpoint that fibers are successfully formed and a coating film comprising a fibrous deposit is efficiently formed on a surface of an object for forming a coating thereon even if spray rate employed at the time of electrostatic spray is high.

Examples of the ester oil include esters each of a straight chain or branched chain fatty acid and a straight chain or branched chain alcohol or polyhydric alcohol. Specific examples include isopropyl myristate, cetyl isooctanoate, isocetyl octanoate, octyldodecyl myristate, isopropyl palmitate, butyl stearate, hexyl laurate, decyl oleate, octyldodecyl oleate, hexadecyl dimethyloctanoate, cetyl lactate, myristyl lactate, lanolin acetate, isocetyl stearate, isocetyl isostearate, ethylhexyl isononanoate, isononyl isononanoate, isotridecyl isononanoate, isostearyl isostearate, cholesteryl 12-hydroxystearate, ethylene glycol di-2-ethylhexanoate, dipentaerythritol fatty acid ester, N-alkyl glycol monoisostearate, propylene glycol dicaprylate, propylene glycol diisostearate, neopentyl glycol dicaprylate, diisostearyl malate, glycerin di-2-heptylundecanoate, trimethylolpropane tri-2-ethylhexanoate, trimethylolpropane triisostearate, pentaerythrit tetra-2-ethylhexanoate, glyceryl tri-2-ethylhexanoate, trimethylolpropane triisostearate, cetyl 2-ethylhexanoate, 2-ethylhexylpalmitate, diethylhexyl naphthalenedicarboxylate, alkyl benzoate (having 12 to 15 carbon atoms), cetearyl isononanoate, glycerin tri(caprylate/caprate), butylene glycol (dicaprylate/caprate), propylene glycol di(caprylate/caprate), glyceryl triisostearate, glyceryl tri-2-heptylundecanoate, glyceryl tricocoate, castor oil fatty acid methyl ester, oleyl oleate, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, 2-ethylhexyl para-methoxycinnamate, and tripropylene glycol dipivalate.

Among these, one selected from the group consisting of octyldodecyl myristate, myristyl myristate, isocetyl stearate, isononyl isononanoate, isocetyl isostearate, cetearyl isononanoate, diisobutyl adipate, di-2-ethylhexyl sebacate, isopropyl myristate, isopropyl palmitate, diisostearyl malate, neopentyl glycol dicaprylate, and glycerin tri(caprylate/caprate) is preferred, at least one selected from the group consisting of isopropyl myristate, isopropyl palmitate, diisostearyl malate, neopentyl glycol dicaprylate, alkyl benzoate (having 12 to 15 carbon atoms), and glycerin tri (caprylate/caprate) is more preferred, and at least one selected from the group consisting of neopentyl glycol dicaprylate, glycerin tri(caprylate/caprate), and diisostearyl malate is further more preferred from the viewpoint that fibers are successfully formed and a coating film comprising a fibrous deposit is efficiently formed on a surface of an object for forming a coating thereon even if spray rate employed at the time of electrostatic spray is high.

As the ester oil, vegetable oils and animal oils containing any one of the ester oils described above can be used, and examples include olive oil, jojoba oil, macadamia nut oil, meadowfoam oil, castor oil, safflower oil, sunflower oil, avocado oil, canola oil, apricot kernel oil, rice germ oil, and rice bran oil.

Examples of the higher alcohol in liquid form include higher alcohols in liquid form having 12 to 20 carbon atoms, higher alcohols containing a branched fatty acid as a composing element are preferred, and specific examples include isostearyl alcohol and oleyl alcohol.

Examples of the hydrocarbon oil in liquid form include liquid paraffin, squalane, squalene, n-octane, n-heptane, cyclohexane, light isoparaffin, liquid isoparaffin, hydrogenated polyisobutene, polybutene, and polyisobutane, and from the viewpoint of use impression, liquid paraffin, light isoparaffin, liquid isoparaffin, squalane, squalene, n-octane, n-heptane, and cyclohexane are preferred, and liquid paraffin and squalane are more preferred.

In the fiber formable composition of the present invention, from the viewpoint that fibers are successfully formed and a coating film comprising a fibrous deposit is efficiently formed on a surface of an object for forming a coating thereon even if spray rate employed at the time of electrostatic spray is high, the mass ratio of Component (c1) to Component (c), ((c1)/(c)), is 0.6 or more, namely, 0.6 or more and 1 or less.

From the viewpoint that fibers are successfully formed and a coating film comprising a fibrous deposit is efficiently formed on a surface of an object for forming a coating thereon even if spray rate employed at the time of electrostatic spray is high, a total content of Component (c) in the fiber formable composition of the present invention is preferably 9% by mass or more and 25% by mass or less, more preferably 10% by mass or more, and more preferably 22% by mass or less, and further more preferably 20% by mass or less. Specifically, the content is preferably 9% by mass or more and 25% by mass or less, more preferably 10% by mass or more and 22% by mass or less, and further more preferably 10% by mass or more and 20% by mass or less.

When the composition of the present invention is used to form a coating film on a surface of an object for forming a coating thereon by an electrostatic spray, even if spray rate is high, fibers are successfully formed, and the coating film comprising a fibrous deposit can be efficiently formed on the surface of the object for forming a coating thereon. In the present invention, spray needs not be always ejected in a mist form, and is expressed as ejection forming fine fibers, namely, ejection at a spinning level. In addition, fibers can be successfully formed even when spray rate (or ejection speed or spinning speed) is 0.12 mL/min or more and 2 mL/min or less, and the spray rate is more preferably 0.15 mL/min or more and 1.5 mL/min or less, and further more preferably 0.15 mL/min or more and 0.7 mL/min or less.

In the fiber formable composition of the present invention, (d) polyol can be further comprised. As the polyol, a polyol being liquid at 25° C. is preferred.

Examples of the polyol include alkylene glycols such as ethylene glycol, propylene glycol, 1,3-propanediol, and 1,3-butanediol; polyalkylene glycols such as diethylene glycol, dipropylene glycol, polyethylene glycol having a molecular weight of 1,000 or less, and polypropylene glycol; and glycerins such as glycerin, diglycerin, and triglycerin. Among these, from the viewpoint that fibers are successfully formed and a coating film comprising a fibrous deposit is efficiently formed on an object for forming a coating thereon even if spray rate employed at the time of electrostatic spray is high, ethylene glycol, propylene glycol, 1,3-butanediol, dipropylene glycol, polyethylene glycol having a molecular weight of 1,000 or less, glycerin, and diglycerin are preferred, propylene glycol, 1,3-butanediol, and glycerin are more preferred, and at least glycerin is further more preferably contained.

A content of Component (d) is preferably 0% by mass or more and 10% by mass or less in the fiber formable composition for the skin from the viewpoint that fibers are successfully formed and a coating film comprising a fibrous deposit is efficiently formed on a surface of an object for forming a coating thereon even if spray rate employed at the time of electrostatic spray is high. The content is preferably 0% by mass or more and 9% by mass or less, more preferably 0% by mass or more and 8% by mass or less, and further more preferably 0% by mass or more and 6% by mass or less.

The fiber formable composition may contain, in addition to the above components, an oil agent other than Components (c), a coloring pigment, an extender pigment, a dye, a fragrance, a repellent, an antioxidant, a stabilizer, a preservative, vitamins, and water.

A viscosity of the fiber formable composition is, from a viewpoint of stably forming a coating film composed of fibers on a surface of an object for forming a coating thereon and a viewpoint of spinning property obtained by an electrostatic spray, drying of fibers, and thinning diameters of fibers, preferably 2 mPa·s or more at 25° C., more preferably 5 mPa·s or more, further more preferably 10 mPa·s or more, further more preferably 30 mPa·s or more, further more preferably 50 mPa·s or more, and even more preferably 80 mPa·s or more. Additionally, it is preferably 2,000 mPa·s or less, more preferably 1,500 mPa·s or less, further more preferably 1,200 mPa·s or less, further more preferably 1,000 mPa·s or less, and even more preferably 800 mPa·s or less. A viscosity of the fiber formable composition ranges preferably 2 mPa·s or more and 2,000 mPa·s or less, more preferably 5 mPa·s or more and 1,500 mPa·s or less, further more preferably 10 mPa·s or more and 1,200 mPa·s or less, further more preferably 30 mPa·s or more and 1,000 mPa·s or less, and even more preferably 50 mPa·s or more and 800 mPa·s or less. A viscosity of the fiber formable composition is measured using a B-type viscometer at 25° C. For the B-type viscometer, for example, a B-type viscometer (TVB-10M) manufactured by Toki Sangyo Co., Ltd. can be used. The measurement condition in such a case has a measurement temperature of 25° C. The measurement temperature herein refers to a temperature of the fiber formable composition. Type of a rotor and a rotation speed of the rotor are selected in accordance with specifications of a measurement apparatus to be used depending on a viscosity of the fiber formable composition. For example, when the above B-type viscometer (TVB-10M) manufactured by Toki Sangyo Co., Ltd. is used, the measurement can be achieved using an M2 rotor at 6 rpm when a viscosity of the fiber formable composition is 2,500 mPa·s or more, an M2 rotor at 12 rpm when such a viscosity is 1,000 mPa·s or more and less than 2,500 mPa·s, an M2 rotor at 30 rpm when such a viscosity is 500 mPa·s or more and less than 1,000 mPa·s, an M2 rotor at 60 rpm when such a viscosity is 100 mPa·s or more and less than 500 mPa·s, and an M1 rotor at 60 rpm when such a viscosity is less than 100 mPa·s. Additionally, instructions for use of the above B-type viscometer (TVB-10M) manufactured by Toki Sangyo Co., Ltd. also include measurement conditions other than the above measurement conditions and a viscosity can also be measured under other measurement conditions depending on a viscosity of the fiber formable composition.

Next, a method for forming a coating film comprising a fibrous deposit on a surface of an object for forming a coating thereon (for example, on a surface of the skin) by an electrostatic spray using the fiber formable composition of the present invention will be described.

In the following, a method for forming a coating film comprising a fibrous deposit directly on a surface of the skin will be described as a preferable embodiment. The method for forming a coating film comprising a fibrous deposit on a surface of the skin encompasses, in addition to directly spraying (spinning) the composition onto the skin surface, a method in which the composition is sprayed onto a transferring tool, such as a transferring puff, a transferring sheet of nonwoven fabric, a fabric base or the like, or transferring cushion material, before transferring the composition to the skin. It notes that examples of the object for forming a coating thereon excluding the skin include a metal base, a resin base, a foaming agent base, a rubber base, a fabric base, a nonwoven fabric base, and a wood base, and among these, a foaming agent base is preferred, and a specific example includes a powder puff.

The fiber formable composition is sprayed, by an electrostatic spray method, directly onto a portion of the object for forming a coating thereon where a coating film is to be formed, for example, a portion on the human skin where a coating film is to be formed. The electrostatic spray method includes a step of electrostatically spraying, with an electrostatic spray apparatus, the fiber formable composition onto a surface of the object for forming a coating thereon. The electrostatic spray apparatus basically has a container for accommodating the above composition, a nozzle for discharging the composition, a feed apparatus for feeding the composition accommodated in the container to the nozzle, and a power supply for applying a voltage to the nozzle.

FIG. 1 is a schematic diagram showing a structure of the electrostatic spray apparatus preferably used in the present invention. An electrostatic spray apparatus 10 shown in the same figure is equipped with a low-voltage power supply 11. The low-voltage power supply 11 is for generating several volts to ten and some volts. The low-voltage power supply 11 is preferably composed of one or more batteries for the purpose of increasing the portability of the electrostatic spray apparatus 10. Additionally, batteries, when used as the low-voltage power supply 11, can be easily replaceable as needed, hence advantageous. Instead of batteries, an AC adapter can also be used as the low-voltage power supply 11.

The electrostatic spray apparatus 10 is also equipped with a high-voltage power supply 12. The high-voltage power supply 12 is connected to the low-voltage power supply 11 and equipped with an electric circuit (not shown) to boost the voltage generated at the low-voltage power supply 11 to a high voltage. A voltage boost electric circuit is generally made up of a transformer, a capacitor, and a semiconductor element.

The electrostatic spray apparatus 10 is further equipped with an auxiliary electric circuit 13. The auxiliary electric circuit 13 is interposed between the low-voltage power supply 11 and the high-voltage power supply 12 described above and functions to adjust a voltage of the low-voltage power supply 11 thereby allowing the high-voltage power supply 12 to operate stably. The auxiliary electric circuit 13 has a function of controlling the rotation speed of a motor equipped by a micro gear pump 14 to be described later. Controlling the rotation speed of the motor controls a feed amount of the fiber formable composition to the micro gear pump 14 from a container 15 for the fiber formable composition. A switch SW is attached between the auxiliary electric circuit 13 and the low-voltage power supply 11 and the electrostatic spray apparatus 10 can start/stop by switching ON-OFF the switch SW.

The electrostatic spray apparatus 10 is further equipped with a nozzle 16. The nozzle 16 is composed of various conductors such as a metal to begin with and non-conductors such as plastic, rubber, and ceramic, and has a shape which can discharge the fiber formable composition from the tip thereof. Inside the nozzle 16, a microspace through which the fiber formable composition passes is formed longitudinally along with the nozzle 16. A cross-sectional size of this microspace is preferably 100 μm or more and 1,000 μm or less when expressed in the diameter.

The nozzle 16 communicates with the micro gear pump 14 via a pipeline 17. The pipeline 17 may be a conductor or a non-conductor. Additionally, the nozzle 16 is electrically connected to the high-voltage power supply 12. This enables the application of a high-voltage to the nozzle 16. In this case, the nozzle 16 and the high-voltage power supply 12 are electrically connected via an electric current limiting resistor 19 to prevent an excess electric current from flowing when a human body directly touches the nozzle 16.

The micro gear pump 14 communicating with the nozzle 16 via the pipeline 17 functions as a feed apparatus for feeding the fiber formable composition accommodated in the container 15 to the nozzle 16. The micro gear pump 14 receives a feed of power supply from the low-voltage power supply 11 and operates. The micro gear pump 14 is configured in such a way as to feed a predetermined amount of the fiber formable composition to the nozzle 16 in response to the control by the auxiliary electric circuit 13.

The container 15 is connected to the micro gear pump 14 via a flexible pipeline 18. In the container 15, the fiber formable composition is accommodated. The container 15 is preferably an exchangeable cartridge type. It is also possible to employ a configuration using a piston pump instead of the micro gear pump 14 in such a way as to feed a predetermined amount of the fiber formable composition to the nozzle 16 in response to the control by the auxiliary electric circuit 13.

Figure 2:
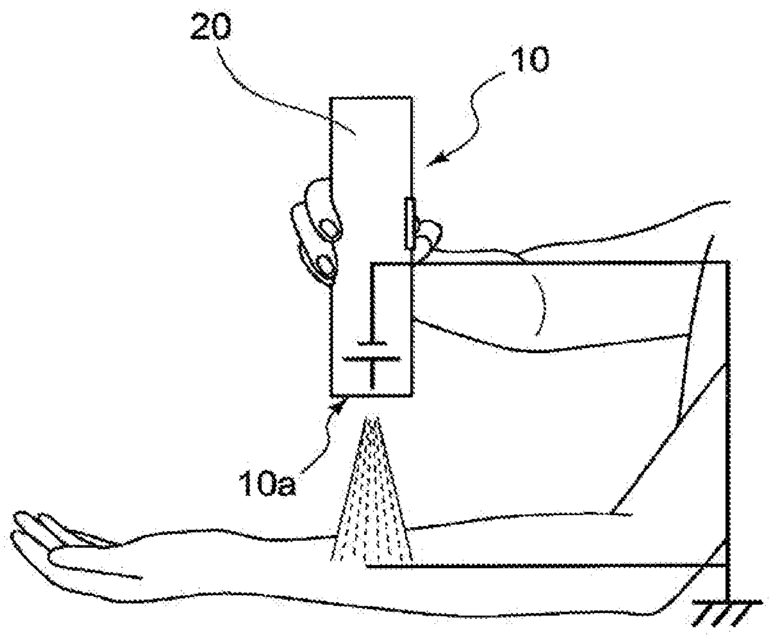
FIG. 2 illustrates a schematic view showing a state in which an electrostatic spray method is performed using the electrostatic spray apparatus.

The electrostatic spray apparatus 10 having the above structure can be used as shown in, for example, FIG. 2. FIG. 2 shows a hand-held electrostatic spray apparatus 10 having a size holdable by one hand. The electrostatic spray apparatus 10 shown in the same figure accommodates all the members of the structural diagram shown in FIG. 1 inside a cylindrical housing 20. The nozzle (not shown) is arranged at an end 10*a* of a longitudinal direction of the housing 20. The nozzle is arranged in the housing 20 with a coming-out direction of the composition in line with the longitudinal direction of the housing 20 so that it protrudes toward the skin side. When the nozzle tip is arranged in such a way as to protrude toward the skin along with the longitudinal direction of the housing 20, the fiber formable composition is less likely to attach to the housing thereby stably forming a coating film.

When operating the electrostatic spray apparatus 10, a user, that is, for example, a person who forms a coating film on a site at which the coating film is formed on the skin by an electrostatic spray, holds the apparatus 10 with a hand and turns the end 10*a* of the apparatus 10 at which the nozzle (not shown) is arranged toward an application site to which an electrostatic spray is carried out. FIG. 2 shows a state in which an end 10*a* of the electrostatic spray apparatus 10 is turned toward the inner side of the user's forearm. In this state, the apparatus 10 is switched ON to carry out the electrostatic spray method. When the apparatus 10 is turned on, an electric field is generated between the nozzle and the skin.

In the embodiment shown in FIG. 2, a positive high voltage is applied to the nozzle thereby making the skin a negative electrode. When the electric field is generated between the nozzle and the skin, the fiber formable composition at the nozzle tip section is polarized due to electrostatic induction and forms a corn shape at the tip part, and droplets of the charged fiber formable composition is discharged into the air from the corn tip toward the skin along with the electric field. As Component (b), a solvent, evaporates from the charged fiber formable composition discharged into the air, the fiber formable composition has an excessed charge density on the surface, proceeds in the air by Coulomb repulsion while repeatedly broken down, and reaches the skin. In this instance, when a viscosity of the fiber formable composition is suitably adjusted, the volatile substance, a solvent, is caused to volatilize from droplets while the composition is discharged into the air, and the polymer having a coating film forming ability, a solute, of Component (a) forms fibers as elongated by a potential difference while solidified, whereby the formed fibers are caused to deposit at an application site. For example, when a viscosity of the fiber formable composition is increased, the composition is likely to deposit at an application site in the form of fibers. Herewith, a porous coating film comprising a fibrous deposit is formed on the surface of an application site. Such a porous coating film comprising a fibrous deposit can also be formed by adjusting the distance between the nozzle and the skin or a voltage to be applied to the nozzle.

A high potential difference is being generated between the nozzle and the skin while carrying out the electrostatic spray method. However, the impedance is so significant that an electric current flowing through the human body is extremely small. For example, the present inventors confirmed that, for example, an electric current flowing through the human body while carrying out the electrostatic spray method is some digits smaller than an electric current flowing through the human body by static electricity generated in daily life.

When fibrous deposits are formed by the electrostatic spray method, a thickness of fibers when expressed by a diameter equivalent to a circle is preferably 10 nm or more, more preferably 50 nm or more, and further more preferably 100 nm or more. Additionally, the thickness is preferably 3,000 nm or less, more preferably 1,500 nm or less, and further more preferably 1,000 nm or less.

The thickness of a fiber can be measured by, for example, magnifying the fibers 10,000 times to observe using a scanning electron microscopic (SEM), excluding defects (fiber masses, fiber overlaps, and droplets) from the twodimensional images, randomly selecting 10 fibers, drawing a line perpendicular to the longitudinal direction of the fibers, and directly reading a diameter of the fibers.

The fiber is a continuous fiber having an unlimited length in production principle, and preferably has a length of at least 100 times or more a thickness of the fiber. In the present Description, a fiber having a length of 100 times or more a thickness of the fiber is defined as the "continuous fiber." The coating film produced by the electrostatic spray method is preferably a porous non-continuous coating film composed of continuous fibrous deposits. The coating film in such a form can be delt with as one sheet as an aggregate, and in addition, has advantages of having a very soft feature, being difficult to fall apart even when a shear force is applied thereto, and being excellent in followability to motion of the body. It also has an advantage of being excellent in dissipation of sweat secreted from the skin. In addition, it also has an advantage of easy peelability. On the contrary, a continuous coating film not having a large number of pores is not easily peeled, and poor in dissipation of sweat, and hence easily makes the skin sweaty.

In the method for producing the fiber formable composition, one may stir a mixed solution containing all components but it is preferable to have Step 1 for stirring Mixed solution 1 containing the components other than Component (a) and subsequently Step 2 for adding Component (a) followed by stirring and mixing. These Step 1 and Step 2 are preferably carried out at normal temperature of 10° C. to 30° C.

A distance between the nozzle and the skin is, depending on a voltage to be applied to the nozzle through, preferably 10 mm or more, more preferably 20 mm or more, and further more preferably 40 mm or more. Additionally, it is preferably 160 mm or less, more preferably 140 mm or less, and further more preferably 120 mm or less. A distance between the nozzle and the skin within this range can enhance the formability of a coating film. A distance between the nozzle and the skin can be measured by a commonly used non-contact sensor.

A basis weight of the coating film is, regardless of the coating film formed by the electrostatic spray method being porous or not, preferably 0.1 g/m$^2$ or more, more preferably 0.2 g/m$^2$ or more, and further more preferably 0.5 g/m$^2$ or more. Additionally, it is preferably 30 g/m$^2$ or less, more preferably 20 g/m$^2$ or less, and further more preferably 10 g/m$^2$ or less. For example, a basis weight of the formed coating film is preferably 0.1 g/m$^2$ or more and 30 g/m$^2$ or less, more preferably 0.2 g/m$^2$ or more and 20 g/m$^2$ or less, and further more preferably 0.5 g/m$^2$ or more and 10 g/m$^2$ or less. When the basis weight of the coating film is thus set, the skin compatibility of the coating film, the adhesion, and the followability of the coating film to the skin, and the durability against moisture can be improved.

In the present invention, a skincare cosmetic or a makeup cosmetic may be applied to the skin before or after the electrostatic spray step for forming a coating film on the skin by an electrostatic spray using the fiber formable composition of the present invention described above.

The skincare cosmetic used herein includes skin lotions, milky lotions, creams, serums (whitening, anti-wrinkle, or the like), all-in-one cosmetics, UV care cosmetics, BB creams, oils, oil gels, and lotions, and the makeup cosmetic includes makeup bases, foundations, concealers, cheek blushers, eye shadows, mascaras, eye liners, eyebrows, overcoat agents, and lipsticks.

Examples of the application means of the above skincare cosmetics or makeup cosmetics to the skin other than the electrostatic spray include application by hands and/or fingers, application using a nonwoven cloth such as cotton, application using a sponge, spraying using a usual spray, spraying mist, steaming, dripping, and sprinkling.

In reference with the embodiments described above, the present invention further discloses the following compositions and methods.

<1> A fiber formable composition for forming a coating film comprising a deposit containing fibers on a surface of an object for forming a coating thereon by an electrostatic spray, the fiber formable composition comprising the following Components (a), (b), and (c):
(a) a polymer having a coating film forming ability;
(b) one or more volatile substances selected from the group consisting of water, an alcohol and a ketone; and
(c) an oil component being liquid at 25° C. and containing (c1) one or more selected from the group consisting of oil components having a surface tension at 25° C. of 25 mN/m or less and being liquid at 25° C., wherein a content of Component (c1) in the entire fiber formable composition is 9% by mass or more and 25% by mass or less, and a mass ratio of Component (c1) to Component (c), ((c1)/(c)), is 0.6 or more.

<2> The fiber formable composition according to <1>, wherein the object for forming a film thereon is the skin.

<3> The fiber formable composition according to <1> or <2>, wherein Component (a) is preferably one or more selected from water-insoluble polymers having a coating film forming ability.

<4> The fiber formable composition according to any one of <1> to <3>, wherein Component (a) is a water-insoluble polymer having a coating film forming ability, and preferably one or more selected from the group consisting of a completely saponified polyvinyl alcohol insolubilizable after forming a coating film, a partially saponified polyvinyl alcohol crosslinkable after forming a coating film when used in combination with a crosslinking agent, an oxazoline-modified silicone such as a poly(N-propanoylethyleneimine)graft-dimethylsiloxane/γ-aminopropylmethylsiloxane copolymer, a polyvinyl acetal diethylamino acetate, Zein (main component of corn protein), a polyester, a polylactic acid (PLA), an acrylic resin such as a polyacrylonitrile resin, and a polymethacrylic acid resin, and a polystyrene resin, a polyvinyl butyral resin, an alkyl acetalized polyvinyl alcohol, a polyethylene terephthalate resin, a polybutylene terephthalate resin, a polyurethane resin, a polyamide resin, a polyimide resin, and a polyamideimide resin, and further more preferably one or more selected from the group consisting of a completely saponified polyvinyl alcohol insolubilizable after forming a coating film, a partially saponified polyvinyl alcohol crosslinkable after forming a coating film when used in combination with a crosslinking agent, a polyvinyl butyral resin, an alkyl acetalized polyvinyl alcohol, a polyurethane resin, an oxazoline-modified silicone, a polyvinyl acetal diethylamino acetate, and Zein.

<5> The fiber formable composition according to any one of <1> to <4>, wherein a content of Component (a) is preferably 4 mass % or more, more preferably 5 mass % or more, further more preferably 6 mass % or more, and even more preferably 8 mass % or more, is preferably 35 mass % or less, more preferably 30 mass % or less, further more preferably 25 mass % or less, and even more preferably 20 mass % or less, and is preferably 4 mass % or more and 30 mass % or less, more preferably 4 mass % or more and 25 mass % or less, further more preferably 6 mass % or more and 25 mass % or less, and even more preferably 8 mass % or more and 20 mass % or less.

<6> The fiber formable composition according to any one of <1> to <5>, wherein a content of Component (a) is 4% by mass or more and 30% by mass or less.

<7> The fiber formable composition according to any one of <1> to <5>, wherein a content of Component (a) is 4% by mass or more and 25% by mass or less.

<8> The fiber formable composition according to any one of <1> to <7>, wherein the alcohol of Component (b) is preferably one or more selected from the group consisting of a monovalent chain fatty alcohol, a monovalent cyclic fatty acid, and a monovalent aromatic alcohol, preferably one or more selected from the group consisting of a straight chain or branched chain monovalent chain fatty alcohol having 1 to 6 carbon atoms, a monovalent cyclic fatty alcohol having 4 to 6 carbon atoms, benzyl alcohol, and phenyl ethyl alcohol, further more preferably one or more selected from the group consisting of ethanol, isopropyl alcohol, n-butyl alcohol, phenyl ethyl alcohol, n-propanol, and n-pentanol.

<9> The fiber formable composition according to any one of <1> to <8>, wherein the ketone of Component (b) is preferably a ketone having two alkyl groups having 1 to 4 carbon atoms, and further more preferably one or more selected from the group consisting of acetone, methyl ethyl ketone, and methyl isobutyl ketone.

<10> The fiber formable composition according to any one of <1> to <9>, wherein Component (b) is preferably one or more selected from the group consisting of water, ethanol, isopropyl alcohol and n-butyl alcohol, more preferably one or more selected from the group consisting of water, ethanol and isopropyl alcohol, further more preferably water and ethanol.

<11> The fiber formable composition according to any one of <1> to <10>, wherein a total content of Component (b) is preferably 30% by mass or more, more preferably 35% by mass or more, further more preferably 40% by mass or more, even more preferably 45% by mass or more, and preferably 87% by mass or less, more preferably 86% by mass or less, further more preferably 84% by mass or less, and even more preferably 82% by mass or less, and is preferably 30% by mass or more and 87% by mass or less, more preferably 35% by mass or more and 86% by mass or less, further more preferably 40% by mass or more and 84% by mass or less, even more preferably 45% by mass or more and 82% by mass or less, and the composition may further comprise 0.4% by mass or more and 10% by mass or less of water with respect to the total content of Component (b).

<12> The fiber formable composition according to any one of <1> to <11>, wherein a total content of Component (b) is 30 mass % or more and 87 mass % or less.

<13> The fiber formable composition according to any one of <1> to <11>, wherein a total content of Component (b) is 35 mass % or more and 86 mass % or less.

<14> The fiber formable composition according to any one of <1> to <13>, wherein a content mass ratio of Component (a) to Component (b), ((a)/(b)), is preferably 0.03 or more, more preferably 0.05 or more, further more preferably 0.08 or more, further more preferably 0.1 or more, and even more preferably 0.12 or more, and preferably 0.6 or less, more preferably 0.45 or less, further more preferably 0.35 or less, further more preferably 0.3 or less, further more preferably 0.25 or less, further more preferably 0.2 or less, and even more preferably 0.18 or less, and preferably 0.05 or more and 0.6 or less, more preferably 0.08 or more and 0.45 or less, further more preferably 0.1 or more and 0.35 or less, further more preferably 0.1 or more and 0.3 or less, and even more preferably 0.12 or more and 0.25 or less.

<15> The fiber formable composition according to any one of <1> to <14>, wherein a mass ratio of Component (a) to Component (b) ((a)/(b)) is 0.05 or more and 0.6 or less.

<16> The fiber formable composition according to any one of <1> to <15>, wherein a mass ratio of Component (a) to Component (b) ((a)/(b)) is 0.08 or more and 0.45 or less.

<17> The fiber formable composition according to any one of <1> to <16>, wherein the surface tension at 25° C. of Component (c1) is preferably 5 mN/m or more and 25 mN/m or less, more preferably 10 mN/m or more and 25 mN/m or less, and further more preferably 10 mN/m or more and 23 mN/m or less.

<18> The fiber formable composition according to any one of <1> to <17>, wherein Component (c1) is preferably a silicone oil having a surface tension at 25° C. of 25 mN/m or less, and more preferably a volatile silicone oil being liquid at 25° C.

<19> The fiber formable composition according to any one of <1> to <18>, a content of Component (c1) in the entire fiber formable composition is preferably 10% by mass or more, and preferably 22% by mass or less, more preferably 20% by mass or less, and specifically, preferably 10% by mass or more and 22% by mass or less, and more preferably 10% by mass or more and 20% by mass or less.

<20> The fiber formable composition according to any one of <1> to <19>, wherein a portion of Component (c) excluding Component (c1) is one or more selected from the group consisting of an ester oil being liquid at 25° C., a hydrocarbon oil being liquid at 25° C., a higher alcohol being liquid at 25° C., and a fatty acid being liquid at 25° C.

<21> The fiber formable composition according to any one of <1> to <20>, wherein a content of Component (c) is preferably 9% by mass or more and 25% by mass or less, more preferably 10% by mass or more, and more preferably 22% by mass or less, further more preferably 20% by mass or less, and specifically, preferably 9% by mass or more and 25% by mass or less, more preferably 10% by mass or more and 22% by mass or less, and further more preferably 10% by mass or more and 20% by mass or less.

<22> The fiber formable composition according to any one of <1> to <21>, further comprising (d) a polyol.

<23> The fiber formable composition according to <22>, wherein a content of Component (d) is, in the fiber formable composition, 0% by mass or more and 10% by mass or less, preferably 0% by mass or more and 9% by mass or less, more preferably 0% by mass or more and 8% by mass or less, and further more preferably 0% by mass or more and 6% by mass or less.

<24> The fiber formable composition according to any one of <1> to <23>, further comprising components selected from the group consisting of a conductivity controlling agent, an oil agent other than Components (c), a coloring pigment, an extender pigment, a dye, a fragrance, a repellent, an antioxidant, a stabilizer, a preservative, a vitamin, and water.

<25> The fiber formable composition according to any one of <1> to <24>, wherein a viscosity of the fiber formable composition at 25° C. is preferably 2 mPa·s or more, more preferably 5 mPa·s or more, further more preferably 10 mPa·s or more, further more preferably 30 mPa·s or more, further more preferably 50 mPa·s or more, and even more preferably 80 mPa·s or more, and preferably 2,000 mPa·s or less, more preferably 1,500 mPa·s or less, further more preferably 1,200 mPa·s or less, further more preferably 1,000 mPa·s or less, further more preferably 800 mPa·s or less, and even more preferably 500 mPa·s or less, and specifically, preferably 2 mPa·s or more and 2,000 mPa·s or less, more preferably 5 mPa·s or more and 1,500 mPa·s or less, further more preferably 10 mPa·s or more and 1,200 mPa·s or less, further more preferably 30 mPa·s or more and 1,000 mPa·s or less, further more preferably 50 mPa·s or more and 800 mPa·s or less, and even more preferably 80 mPa·s or more and 500 mPa·s or less.

<26> The fiber formable composition according to any one of <1> to <25>, used in combination with a cosmetic applied to the skin by a device other than an electrostatic spray.

<27> The fiber formable composition according to <26>, wherein the cosmetic is preferably a skincare cosmetic or a makeup cosmetic.

<28> The fiber formable composition according to any one of <1> to <27>, being a fiber formable composition for the skin.

<29> The fiber formable composition according to any one of <1> to <28>, wherein the (a) polymer having a coating film forming ability is a substance soluble in Component (b).

<30> The fiber formable composition according to any one of <1> to <29>, wherein spray rate employed in the electrostatic spray is preferably 0.12 mL/min or more and 2 mL/min or less, more preferably 0.15 mL/min or more and 1.5 mL/min or less, and further more preferably 0.15 mL/min or more and 0.7 mL/min or less.

<31> A method for producing a coating film, comprising forming a coating film comprising a deposit containing fibers on a surface of an object for forming a coating thereon by an electrostatic spray using a composition comprising the following Components (a), (b), and (c):

(a) a polymer having a coating film forming ability;

(b) one or more volatile substances selected from the group consisting of water, an alcohol and a ketone; and (c) an oil component being liquid at 25° C. and containing (c1) one or more selected from the group consisting of oil components having a surface tension at 25° C. of 25 mN/m or less and being liquid at 25° C., wherein a content of Component (c1) in the entire fiber formable composition is 9% by mass or more and 25% by mass or less, and a mass ratio of Component (c1) to Component (c), ((c1)/(c)), is 0.6 or more.

<32> The method for producing a coating film according to <31>, wherein the object for forming a coating thereon is the skin.

<33> The method for producing a coating film according to <31> or <32>, wherein spray rate employed in the electrostatic spray is preferably 0.12 mL/min or more and 2 mL/min or less, more preferably 0.15 mL/min or more and 1.5 mL/min or less, and further more preferably 0.15 mL/min or more and 0.7 mL/min or less.

EXAMPLES

Hereinafter, the present invention is described in more detail in reference to Examples. However, the scope of the present invention is not limited to these Examples. "%" means "mass %" unless otherwise specified.

Test Example 1

Examples 1 to 18, Comparative Examples 1 to 3

(1) Preparation of the Fiber Formable Composition

Polyvinyl butyral (manufactured by Sekisui Chemical Co., Ltd.: tradename; S-LEC B BM-1) was used as Component (a) and 99.5% ethanol (manufactured by Wako Pure Chemical Corporation) was used as Component (b) for a fiber formable composition. Components shown in Tables 1 and 2 were respectively used as Component (c). Propylene glycol was used as Component (d). The content of each component shown in Tables 1 and 2 is an effective amount and the unit is mass %.

(2) Electrostatic Spray Step

A state of each film obtained by an electrostatic spray onto an aluminum foil for a prescribed time period using an electrostatic spray apparatus 10 having a structure illustrated in FIG. 1 and an appearance illustrated in FIG. 2 was observed.

Device voltage: 14.5 kV

Environment: 30° C. and a humidity of 50%

Distance between nozzle and aluminum foil: from 8 to 10 cm

Aluminum foil: Nippaku foil (manufactured by Mitsubishi Aluminum Co., Ltd.)

A spinning time was set to 27 seconds when a spinning speed was 0.1 mL/min, set to 15 seconds when the spinning speed was 0.4 mL/min, and set to 12 seconds when the spinning speed was 0.5 mL/min.

Evaluation criteria are as follows:

A: Spinning property is good.

B: The composition can be spun but the resultant is fluffy.

C: The composition can be formed into fibers but partly into droplets.

D: The composition is dominantly formed into droplets.

TABLE 1

| | | | Example 1 | Example 2 | Example 3 | Example 4 | Example 5 | Example 6 | Example 7 | Example 8 |
|---|---|---|---|---|---|---|---|---|---|---|
| | (a) | Polyvinyl Butyral Resin *1 | 12 | 12 | 12 | 12 | 12 | 12 | 12 | 12 |
| | (b) | Ethanol *2 | 76 | 73 | 68 | 63 | 73 | 71 | 67 | 64 |
| (c) | (c1) | Methyl Trimethicone *3 | 0 | 10 | 15 | 20 | 0 | 0 | 12 | 15 |
| | | Dimethyl Polysiloxane 0.65 cs *4 | 0 | 0 | 0 | 0 | 0 | 0 | 0 | 0 |
| | | Dimethyl Polysiloxane 1 cs*5 | 0 | 0 | 0 | 0 | 0 | 0 | 0 | 0 |

TABLE 1-continued

| | | | | | | | | | |
|---|---|---|---|---|---|---|---|---|---|
| | Dimethyl Polysiloxane 1.5 cs*6 | 0 | 0 | 0 | 0 | 0 | 0 | 0 | 0 |
| | Dimethyl Polysiloxane 2 cs*7 | 0 | 0 | 0 | 0 | 10 | 12 | 0 | 0 |
| | Dimethyl Polysiloxane 5 cs*8 | 0 | 0 | 0 | 0 | 0 | 0 | 0 | 0 |
| | Dimethyl Polysiloxane 6 cs*9 | 12 | 0 | 0 | 0 | 0 | 0 | 0 | 0 |
| | Neopentyl Glycol Dicaprylate *10 | 0 | 0 | 0 | 0 | 0 | 0 | 4 | 4 |
| | Diisostearyl Malate *11 | 0 | 0 | 0 | 0 | 0 | 0 | 0 | 0 |
| (d) | Propylene Glycol (PPG-7)*12 | 0 | 5 | 5 | 5 | 5 | 5 | 5 | 5 |
| | Total | 100 | 100 | 100 | 100 | 100 | 100 | 100 | 100 |
| Evaluation | 0.1 ml/min Fibers Formed or Not | A | A | A | A | A | A | A | A |
| | 0.4 ml/min Fibers Formed or Not | A | A | A | A | A | A | A | A |
| | 0.5 ml/min Fibers Formed or Not | A | B | A | A | A | A | A | A |

| | | | Example 9 | Example 10 | Example 11 | Comparative Example 1 | Comparative Example 2 | Comparative Example 3 |
|---|---|---|---|---|---|---|---|---|
| | (a) | Polyvinyl Butyral Resin *1 | 12 | 12 | 12 | 12 | 12 | 12 |
| | (b) | Ethanol *2 | 69 | 69 | 69 | 63 | 80 | 77 |
| (c) | (c1) | Methyl Trimethicone *3 | 0 | 0 | 0 | 0 | 0 | 6 |
| | | Dimethyl Polysiloxane 0.65 cs *4 | 0 | 0 | 0 | 0 | 0 | 0 |
| | | Dimethyl Polysiloxane 1 cs*5 | 12 | 0 | 0 | 0 | 0 | 0 |
| | | Dimethyl Polysiloxane 1.5 cs*6 | 0 | 0 | 0 | 0 | 0 | 0 |
| | | Dimethyl Polysiloxane 2 cs*7 | 0 | 12 | 0 | 10 | 0 | 0 |
| | | Dimethyl Polysiloxane 5 cs*8 | 0 | 0 | 12 | 0 | 0 | 0 |
| | | Dimethyl Polysiloxane 6 cs*9 | 0 | 0 | 0 | 0 | 8 | 0 |
| | | Neopentyl Glycol Dicaprylate *10 | 2 | 2 | 2 | 0 | 0 | 0 |
| | | Diisostearyl Malate *11 | 0 | 0 | 0 | 10 | 0 | 0 |
| | (d) | Propylene Glycol (PPG-7)*12 | 5 | 5 | 5 | 5 | 0 | 5 |
| | | Total | 100 | 100 | 100 | 100 | 100 | 100 |
| | Evaluation | 0.1 ml/min Fibers Formed or Not | A | A | A | D | A | A |
| | | 0.4 ml/min Fibers Formed or Not | A | A | A | D | C | C |
| | | 0.5 ml/min Fibers Formed or Not | A | A | A | D | C | C |

TABLE 2

| | | | Example 12 | Example 13 | Example 14 | Example 15 | Example 16 | Example 17 | Example 18 |
|---|---|---|---|---|---|---|---|---|---|
| | (a) | Polyvinyl Butyral Resin *1 | 12 | 12 | 12 | 12 | 12 | 12 | 12 |
| | (b) | Ethanol *2 | 67 | 67 | 67 | 67 | 65 | 63 | 61 |
| (c) | (c1) | Methyl Trimethicone *3 | 0 | 0 | 0 | 0 | 0 | 0 | 0 |
| | | Dimethyl Polysiloxane 0.65 cs *4 | 12 | 0 | 0 | 0 | 0 | 0 | 0 |
| | | Dimethyl Polysiloxane 1 cs*5 | 0 | 12 | 0 | 0 | 12 | 14 | 16 |
| | | Dimethyl Polysiloxane 1.5 cs*6 | 0 | 0 | 0 | 0 | 0 | 0 | 0 |
| | | Dimethyl Polysiloxane 2 cs*7 | 0 | 0 | 12 | 0 | 4 | 4 | 4 |
| | | Dimethyl Polysiloxane 5 cs*8 | 0 | 0 | 0 | 12 | 0 | 0 | 0 |
| | | Dimethyl Polysiloxane 6 cs*9 | 2 | 2 | 2 | 2 | 0 | 0 | 0 |
| | | Neopentyl Glycol Dicaprylate *10 | 2 | 2 | 2 | 2 | 2 | 2 | 2 |
| | | Diisostearyl Malate *11 | 0 | 0 | 0 | 0 | 0 | 0 | 0 |
| | (d) | Propylene Glycol (PPG-7)*12 | 5 | 5 | 5 | 5 | 5 | 5 | 5 |
| | | Total | 100 | 100 | 100 | 100 | 100 | 100 | 100 |
| | Evaluation | 0.1 ml/min Fibers Formed or Not | A | A | A | A | A | A | A |
| | | 0.4 ml/min Fibers Formed or Not | A | A | A | A | A | A | A |
| | | 0.5 ml/min Fibers Formed or Not | A | B | A | A | A | A | A |

*1) S-LEC B BM-01 (manufactured by Sekisui Chemical Co., Ltd.)

*2) 99.5% Ethanol (manufactured by Wako Pure Chemical Industries Ltd.)

*3) TMF-1.5 (manufactured by Shin-Etsu Chemical Co., Ltd.)

*4) KF-96L-0.65CS (manufactured by Shin-Etsu Chemical Co., Ltd.)

*5) KF-96L-1CS (manufactured by Shin-Etsu Chemical Co., Ltd.)

*6) KF-96L-1.5CS (manufactured by Shin-Etsu Chemical Co., Ltd.)

*7) KF-96L-2CS (manufactured by Shin-Etsu Chemical Co., Ltd.)

*8) KF-96L-5CS (manufactured by Shin-Etsu Chemical Co., Ltd.)

*9) KF-96A-6CS (manufactured by Shin-Etsu Chemical Co., Ltd.)

*10) Estemol N-01 (manufactured by The Nisshin OilliO Group, Ltd.)

*11) HAIMALATE DIS (manufactured by Kokyu Alcohol Kogyo Co., Ltd.)

*12) Carpol DL-30 (manufactured by ADEKA Corporation)

It understood from Tables 1 and 2 that fibers are successfully formed and a coating film comprising a fibrous deposit can be efficiently formed on an object for forming a coating thereon even if spray rate employed at the time of an electrostatic spray is high when a fiber formable composition contains, in addition to (a) a polymer having a coating film forming ability and (b) one or more volatile substances selected from the group consisting of water, an alcohol, and ketone, (c) an oil component being liquid at 25° C. and containing (c1) one or more selected from the group consisting of oil components having a surface tension at 25° C. of 25 mN/m or less and being liquid at 25° C., in such a manner as to have a content of Component (c1) in the entire fiber formable composition of 9% by mass or more and 25% by mass or less, and have a mass ratio of Component (c1) to Component (c) ((c1)/(c)) of 0.6 or more.

REFERENCE SIGNS LIST

10 Electrostatic spray apparatus
11 Low-voltage power supply
12 High-voltage power supply
13 Auxiliary electric circuit
14 Micro gear pump
15 Container
16 Nozzle
17 Pipeline
18 Flexible pipeline
19 Electric current limiting resistor
20 Housing

The invention claimed is:

1. A method for producing a coating film, comprising forming a coating film comprising a deposit containing fibers on a surface of an object for forming a coating thereon by an electrostatic spray of a composition comprising the following components (a), (b), and (c):

(a) a polymer having a coating film forming ability;

(b) one or more volatile substances selected from the group consisting of water, an alcohol and a ketone; and (c) an oil component being liquid at 25° C. and containing a component (c1) one or more selected from the group consisting of oil components having a surface tension at 25° C. of 25 mN/m or less and being liquid at 25° C., wherein a content of the component (c1) in the composition is 9% by mass or more and 25% by mass or less, based on a total mass of the composition, and a mass ratio of the component (c1) to the component (c), ((c1)/(c)), is 0.6 or more.

2. The method for producing a coating film according to claim 1, wherein the object for forming a coating thereon is a skin.

3. The method for producing a coating film according to claim 1, wherein a spray rate of the electrostatic spray is 0.12 mL/min or more and 2 mL/min or less.

4. A fiber formable composition for forming a coating film comprising a deposit containing fibers on a surface of an object for forming a coating thereon by an electrostatic spray, wherein the fiber formable composition comprises the following components (a), (b), and (c):

(a) a polymer having a coating film forming ability;

(b) one or more volatile substances selected from the group consisting of water, an alcohol and a ketone; and (c) an oil component being liquid at 25° C. and containing a component (c1) one or more selected from the group consisting of oil components having a surface tension at 25° C. of 25 mN/m or less and being liquid at 25° C., wherein a content of the component (c1) in the fiber formable composition is 9% by mass or more and 25% by mass or less, based on total mass of the fiber formable composition, and a mass ratio of the component (c1) to the component (c), ((c1)/(c)), is 0.6 or more.

5. The fiber formable composition according to claim 4, wherein the object for forming a coating thereon is a skin.

6. The fiber formable composition according to claim 4, wherein the component (c1) is a silicone oil being liquid at 25° C.

7. The fiber formable composition according to claim 4, wherein the component (c1) is a volatile silicone oil being liquid at 25° C.

8. The fiber formable composition according to claim 4, wherein a content of the component (a) is 4% by mass or more and 35% by mass or less, and a content of the component (b) is 45% by mass or more and 95% by mass or less.

9. The fiber formable composition according to claim 4, wherein a mass ratio of the component (a) to the component (b), ((a)/(b)), is 0.03 or more and 0.6 or less.

10. The fiber formable composition according to claim 4, further comprising (d) a polyol.

11. The fiber formable composition according to claim 10, wherein a content of the (d) polyol is 10% by mass or less.

12. The fiber formable composition according to claim 4, wherein the component (a) is soluble in the component (b).

13. The fiber formable composition according to claim 4, wherein the component (a) polymer having a coating film forming ability is at least one selected from the group consisting of a partially saponified polyvinyl alcohol, a low saponified polyvinyl alcohol, a completely saponified polyvinyl alcohol, a polyvinyl butyral resin, a polyurethane resin, a polymethacrylic acid resin, an oxazoline-modified silicone, a polyvinyl acetal diethylamino acetate, and a polylactic acid.

14. The fiber formable composition according to claim 4, wherein a spray rate of the electrostatic spray is 0.12 mL/min or more and 2 mL/min or less.

* * * * *